(12) United States Patent
Fernandez

(10) Patent No.: US 7,637,928 B2
(45) Date of Patent: Dec. 29, 2009

(54) VARIABLE ANGLE LOCKED BONE FIXATION SYSTEM

(75) Inventor: Alberto Angel Fernandez, Montevideo (UY)

(73) Assignee: Synthes USA, LLC, West Chester, PA (US)

( * ) Notice: Subject to any disclaimer, the term of this patent is extended or adjusted under 35 U.S.C. 154(b) by 593 days.

(21) Appl. No.: 10/763,689

(22) Filed: Jan. 26, 2004

(65) Prior Publication Data

US 2005/0165400 A1    Jul. 28, 2005

(51) Int. Cl.
*A61B 17/80* (2006.01)

(52) U.S. Cl. ..................................... 606/289
(58) Field of Classification Search ............... 606/69, 606/70, 71, 72, 73
See application file for complete search history.

(56) References Cited

U.S. PATENT DOCUMENTS

| | | | |
|---|---|---|---|
| 3,741,205 A * | 6/1973 | Markolf et al. ............... 606/61 |
| 4,175,555 A * | 11/1979 | Herbert ...................... 606/73 |
| 4,484,570 A | 11/1984 | Sutter et al. |
| 4,858,601 A * | 8/1989 | Glisson ...................... 606/73 |
| 5,053,036 A | 10/1991 | Perren et al. |
| 5,151,103 A | 9/1992 | Tepic et al. |
| 5,269,784 A | 12/1993 | Mast |
| 5,360,448 A * | 11/1994 | Thramann ................... 606/60 |
| 5,607,426 A | 3/1997 | Ralph et al. |
| 5,709,686 A * | 1/1998 | Talos et al. ................. 606/69 |
| 5,954,722 A | 9/1999 | Bono |
| 6,423,064 B1 | 7/2002 | Kluger |
| 6,454,769 B2 | 9/2002 | Wagner et al. |
| 6,454,770 B1 | 9/2002 | Klaue |
| 6,565,569 B1 | 5/2003 | Assaker et al. |
| 6,575,975 B2 | 6/2003 | Brace et al. |
| 6,623,486 B1 | 9/2003 | Weaver et al. |
| 7,044,953 B2 * | 5/2006 | Capanni ...................... 606/73 |
| 2004/0073218 A1 | 4/2004 | Dahners |
| 2006/0004361 A1 | 1/2006 | Hayeck et al. |

FOREIGN PATENT DOCUMENTS

| | | |
|---|---|---|
| DE | 203 17 651 | 4/2004 |
| EP | 1 604 619 | 12/2005 |
| EP | 1 767 160 | 3/2007 |

* cited by examiner

*Primary Examiner*—Anu Ramana
(74) *Attorney, Agent, or Firm*—Fay Kaplun & Marcin, LLP

(57) ABSTRACT

A bone fixation system including a fixation device having an upper surface, a lower surface and at least one opening extending therethrough and defining a first axis substantially perpendicular to the upper surface, the opening including a plurality of isolated protrusions formed on an inner surface thereof and a bone engaging member insertable through the opening at a selected angle of orientation relative to the first axis, the bone engaging member having a threaded head portion, wherein upon tightening of the bone engaging member, the threaded head portion of the bone engaging member mates with one or more protrusions of the opening to lock the bone engaging member to the plate at the selected angle of orientation relative to the first axis, and wherein the protrusions exhibit the same pitch as the threads on the bone engaging member prior to insertion of the bone engaging member in the opening.

37 Claims, 10 Drawing Sheets

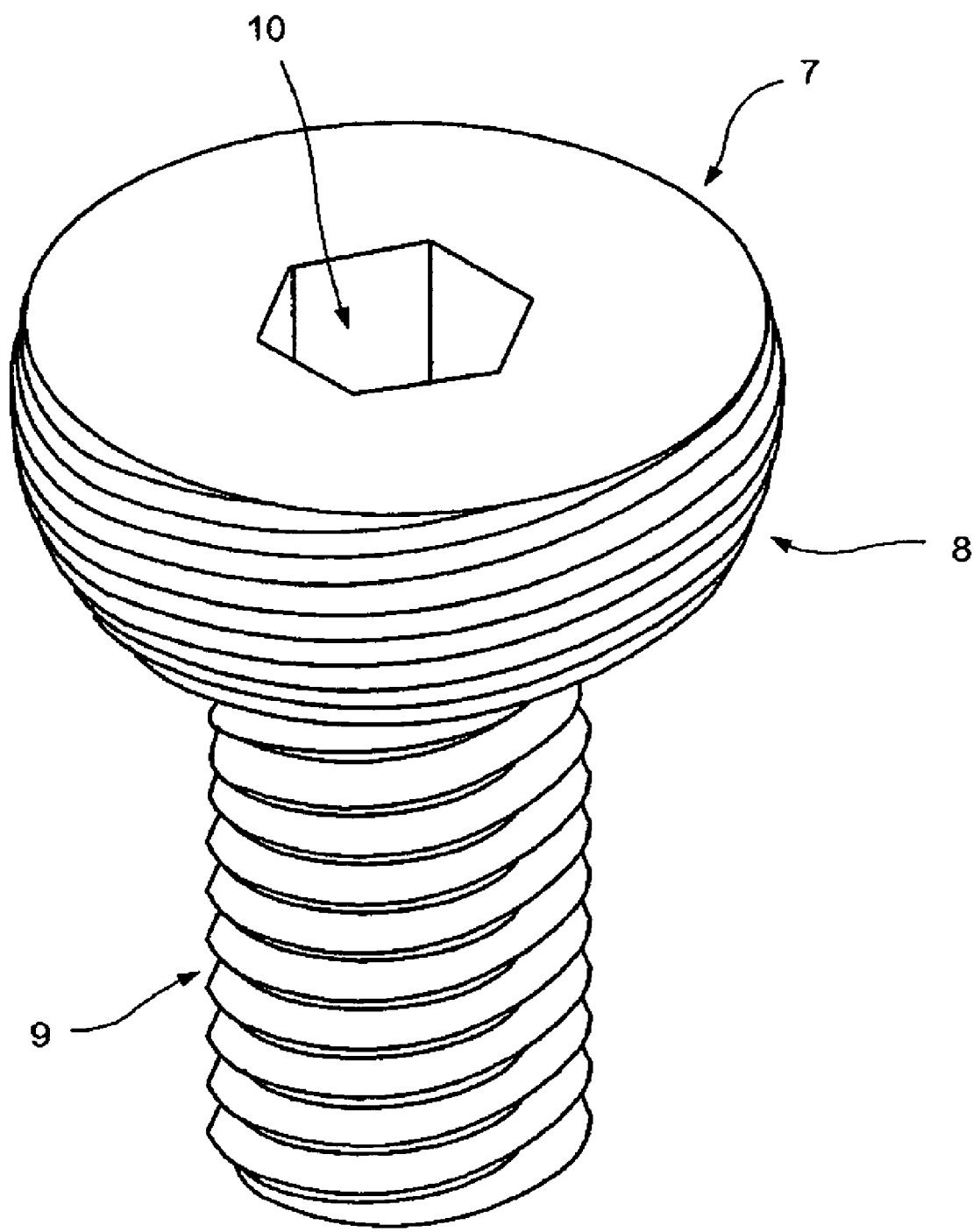
F I G. 2

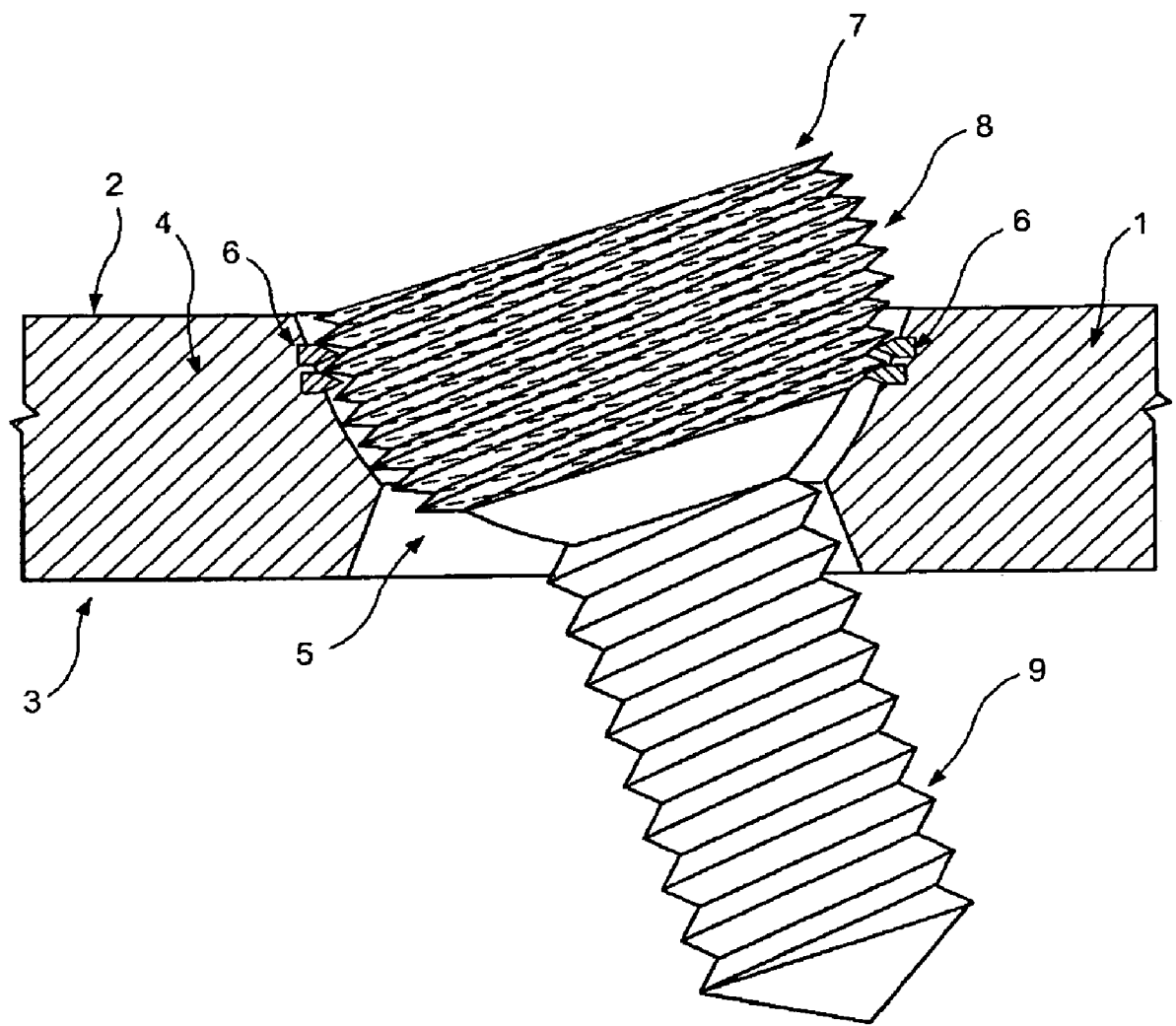
F I G. 10

VARIABLE ANGLE LOCKED BONE FIXATION SYSTEM

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable

BACKGROUND OF THE INVENTION

The present invention is directed to a locked bone fixation assembly, and in particular to an assembly that allows for a surgeon-selected angle of the bone screw relative to the fixation device.

Orthopedic fixation devices, both internal and external, are frequently coupled to bone by the use of fasteners such as screws, threaded bolts or pins. For example, bone plates can be secured to bone with bone screws, inserted through plate holes. Securing the screws to the plate provides a fixed angle relationship between the plate and screw and reduces the incidence of loosening. One method of securing the screw to the plate involves the use of so-called "expansion-head screws." U.S. Pat. No. 4,484,570 discloses an expansion-head screw with a head that has a recess, the walls of which contain a number of slits. After the expansion-head screw is inserted into bone through a hole in the fixation device, a locking screw is inserted into the recess to expand the walls of the recess to thereby lock the screw to the fixation device (such as a plate, internal fixator, nail, or rod). Another method of securing the screw to the plate involves the use of conical heads as shown in U.S. Pat. No. 5,053,036, which discloses conical screw holes, adapted to receive screws having conical heads of a predetermined cone angle, such that the plate will not slide down the heads of the screws. A third method of securing the screw to the plate involves the use of so-called "locking screws." A locking screw has threading on an outer surface of its head that matches with corresponding threading on the surface of a plate hole to lock the screw to the plate. Bone plates having threaded holes for accommodating locking screws are known.

In addition to securing the screw to the fixation device, it is also often desirable to insert the screws at an angle relative to the fixation device selected by the surgeon. The prior art discloses a number of these so-called "polyaxial" systems, most of which utilize a bushing located in a hole in the fixation device to provide for locking at different degrees of angulation of the screw relative to the fixation device. For example, U.S. Pat. No. 5,954,722 discloses a polyaxial (selected variable axis) locking plate that includes a plate hole having a bushing rotatable within the hole. As a screw is being inserted into bone through the bushing and plate hole, a threaded tapered head of the screw engages a threaded internal surface of the bushing to expand the bushing against the wall of the plate hole, thereby friction locking the screw at the desired angular orientation with respect to the plate. U.S. Pat. No 6,575,975 discloses a polyaxial locking plate that includes a plate hole, having a bushing rotatable within the hole, a fastening screw and a locking screw. The head of the fastening screw includes a radial wall that allows for outward expansion so that outwardly expanding the sidewall of the bushing so that the fastening screw is locked to the bushing and fixation device.

Some others of the so-called "polyaxial" systems utilize a ring located in a hole in the fixation device. For example, U.S. Pat. No 6,454,769 discloses a plate system and method of fixation comprising a bone plate, a bone screw and a ring, said ring being expandable against the bone plate to fix the bone screw at a selected angle relative to the bone plate.

These multi-component traditional plate assemblies can be cumbersome and tedious to manipulate during surgery to achieve the most desirable angle for directing the bone screw into the patient.

The present invention relates to an improved locked bone fixation assembly that allows for a surgeon-selected angle of a bone screw relative to the fixation device in only one single surgical action and using only two components, plate and screws, so that no rings, bushing or expansion head screws are longer needed.

BRIEF SUMMARY OF THE INVENTION

Is therefore an object of the present invention to provide a simple effective and strong locking mechanism for locking the bone screw to the fixation device.

Another object of the present invention is to provide a new and novel method of fixation, having a polyaxial coupling of the screw to the fixation device, whereby a single fixation device is compatible with a wide range of screw-in angles.

Further, it is an object of the present invention to provide a method of bone fixation, which provides the surgeon with the greatest freedom to choose the most desirable angle to direct the bone screw while maintaining an effective locking mechanism.

The present invention by being an easy and straightforward procedure for the surgeon makes bone fixation simple and fast overcoming one of the most important subject of matter of actual surgery, time shortening.

By fulfilling the recently mentioned objects, the present invention is extremely helpful to the medical care area.

The preferred embodiment of the present invention provides: a bone fixation device with through hole with an hourglass shape, made by the combination of a partial sphere and two frustoconical holes, to which a number of isolated protrusions are coupled into; a bone screw with a threaded shank and a threaded head shaped as a partial sphere; wherein the bone screw can be threaded into the bone through the hole of the fixation device in only one single surgical action, solidly locking itself against the protrusions of the inner wall of the hole of the fixation device after being tightened; and wherein said bone screw can be inserted through the bore hole of the fixation device at variable orientations. The bone screw has an insertion/extraction hole on which the insertion/extraction tool is connected for the insertion/extraction of the bone screw into/from the bone, through the plate hole.

Other objects, advantages and novel features of the present invention will become apparent from the following detailed description of the invention when considered in conjunction with the accompanying drawings.

BRIEF DESCRIPTION OF THE SEVERAL VIEWS OF THE DRAWINGS

Preferred features of the present invention are disclosed in the accompanying drawings, wherein similar reference characters denote similar elements throughout the several views, and wherein:

FIG. 2 is a perspective view of a spherical headed screw.

FIG. 10 is a front view of a bone fixation assembly according to the present invention wherein the screw is locked at a tilt, and wherein the anterior half of the plate has been removed to allow a better view of the locking system

DETAILED DESCRIPTION OF THE INVENTION

Hereinafter, a method of bone fixation according to the preferred embodiment of the present invention will be explained with reference to FIGS. 1-10.

Figure 1:
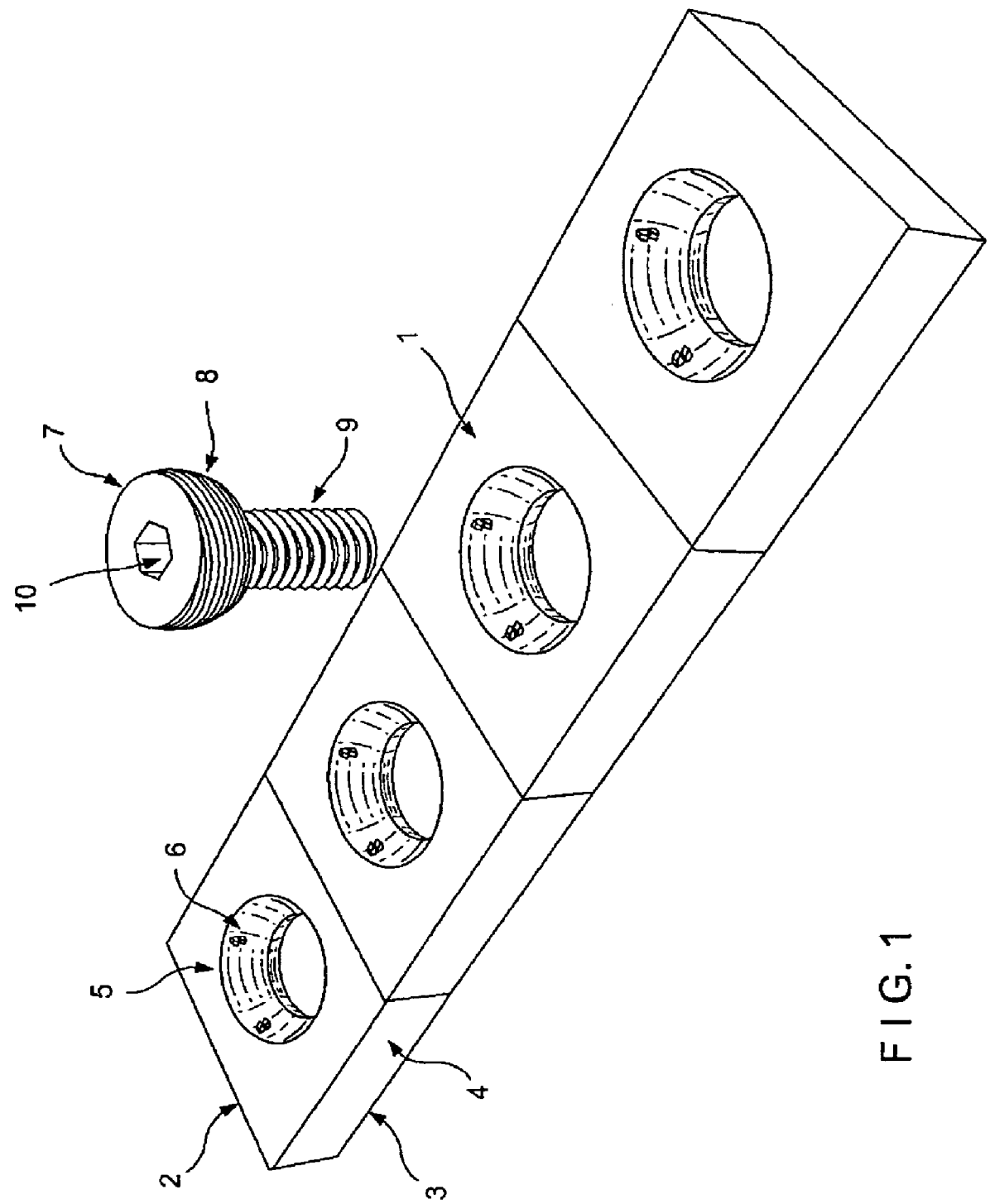
FIG. 1 shows a perspective view of a bone fixation assembly according to the present invention wherein a bone plate having four holes and a threaded spherical screw are shown prior to insertion of the screw through the bone plate.

The bone plate 1 shown in FIG. 1 comprises substantially an upper side 2 and a lower side 3 intended to be closer to the bone than the upper side 2, and a number of plate holes 5 that extend from upper 2 side to lower side 3.

As best shown in FIG. 2, the screws 7 have a head 8 and a shank 9. The head 8 is shaped like a sphere and is threaded with a constant pitch substantially equal to the pitch of the threaded shank 9, and wherein an insertion/extraction hole 1 0 is cut for the connection of the insertion/extraction tool. The thread cut in the screw head 8 has a double entry, keeping substantially the same pitch of the thread of the shank 9. The thread profile may vary according to the requirements and according to the mechanical properties of the used alloy.

Figure 3:
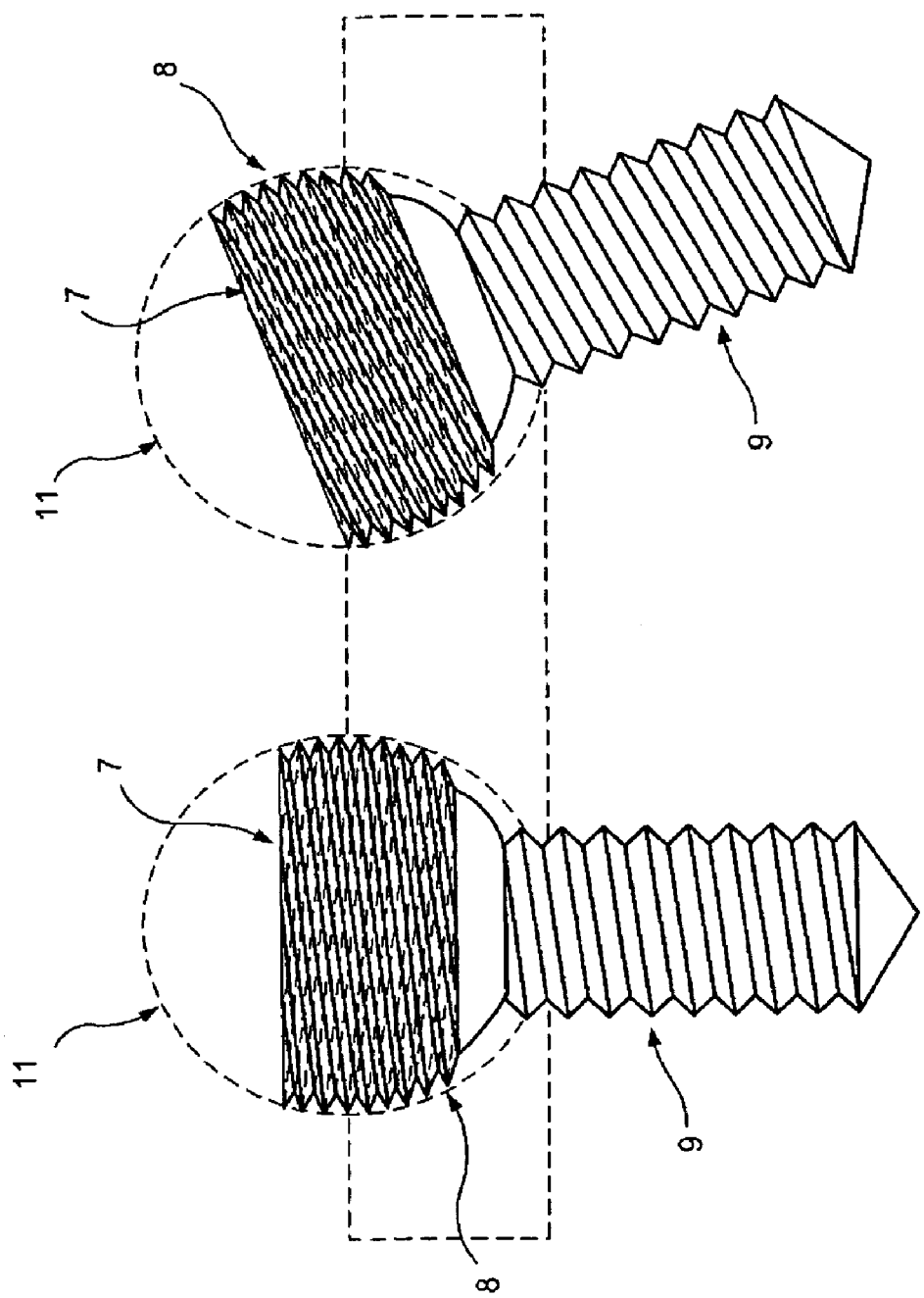
FIG. 3 is a front view of a bone fixation assembly according to the present invention with two separated screws, each of which locks in a different angle with respect to the plate, and wherein the bone plate was removed to best show the locking position of the screw.

FIG. 3 shows a circle 11 as a projection of the sphere from where the thread at the screw head 8 was cut showing that the angle of the screw 7 with respect to the bone plate 1 does not affect the position of the thread of the screw head 8 with respect to the walls of the plate hole 5.

Figure 4:
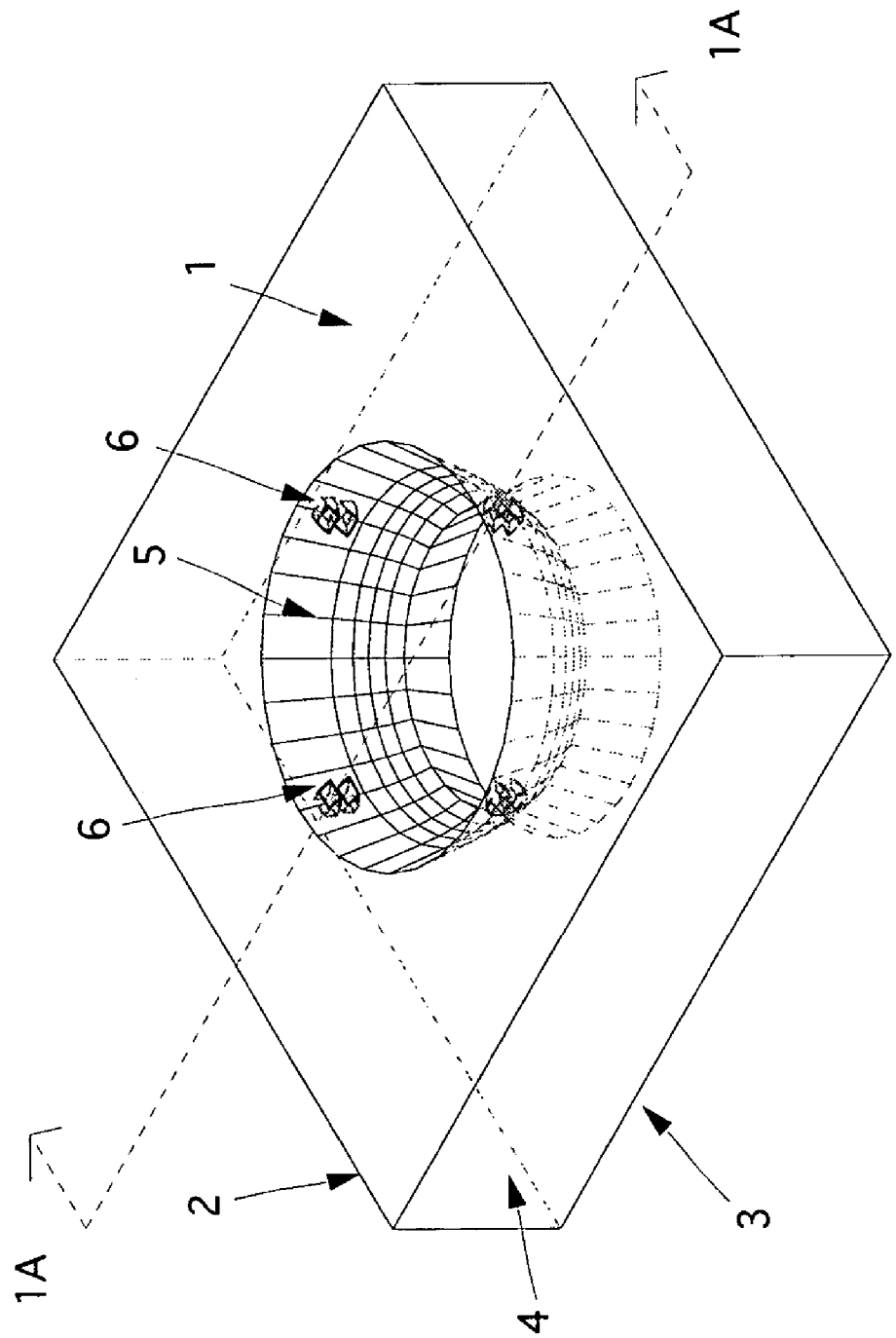
FIG. 4 is a perspective view of a plate hole according to the present invention.
Figure 5:
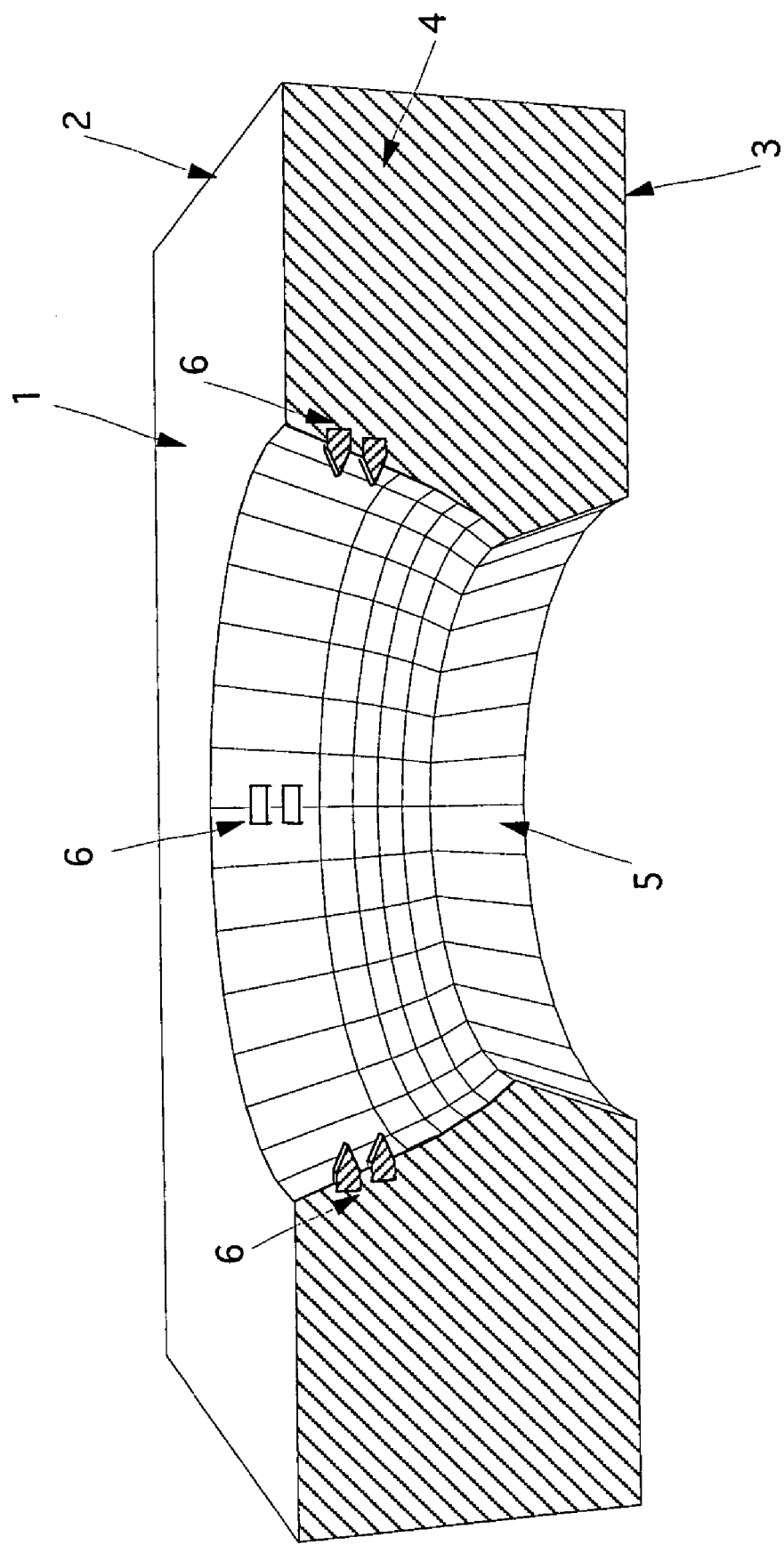
FIG. 5 is a perspective sectional view, at 1A-1A of FIG. 4, of the plate hole.
Figure 6:
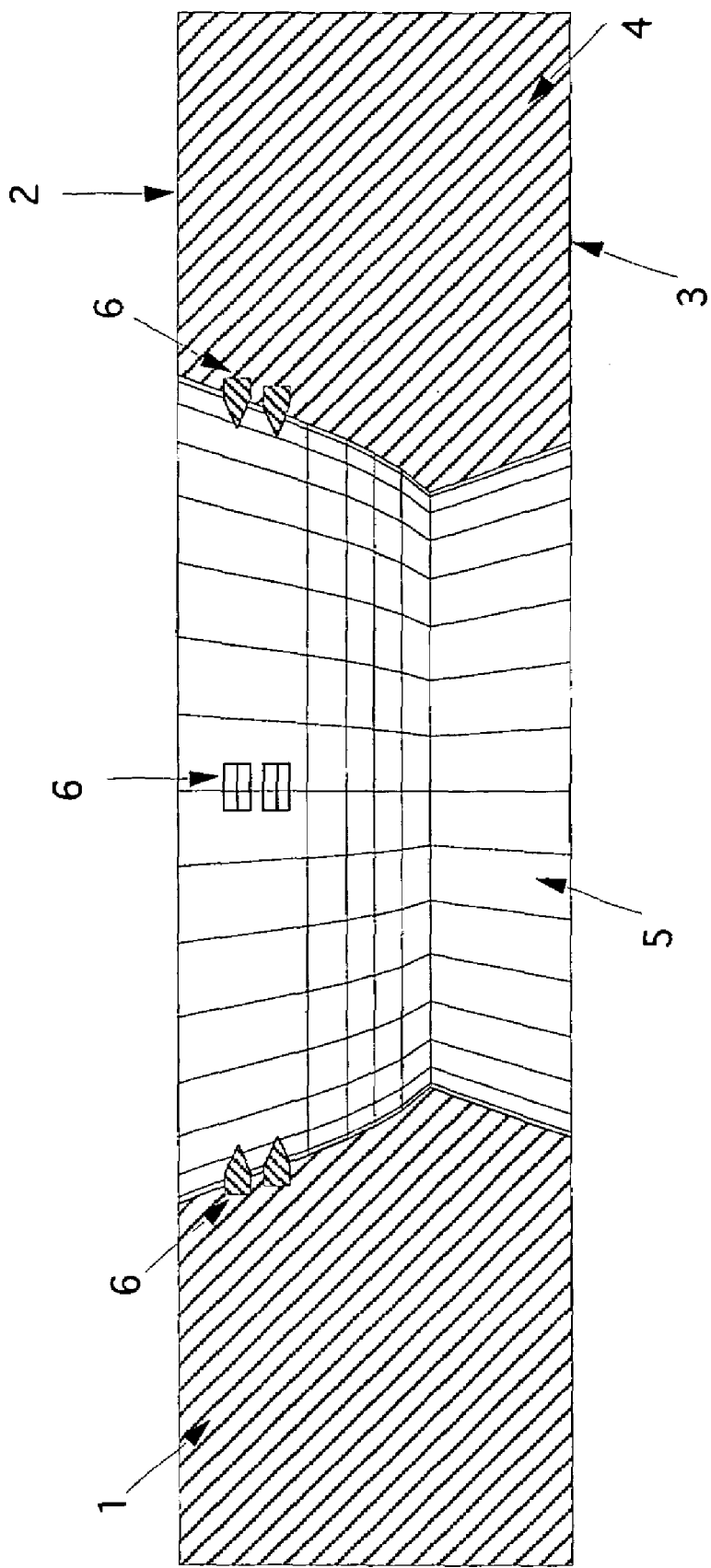
FIG. 6 is a front sectional view, at 1A-1A of FIG. 4, of the plate hole.
Figure 7:
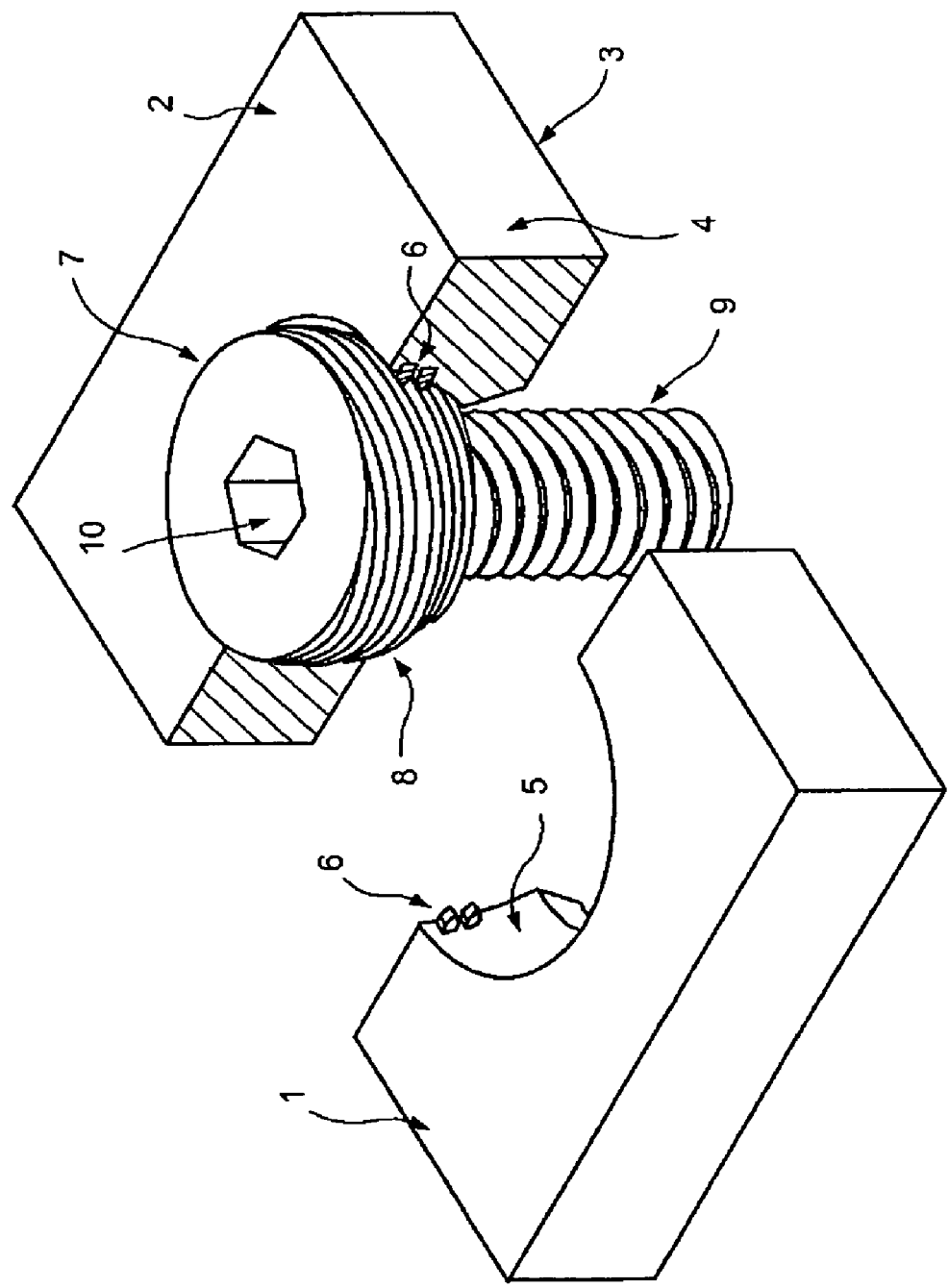
FIG. 7 is a perspective view of a bone fixation assembly according to the present invention wherein the screw is perpendicularly locked to the bone plate, and wherein the anterior half of the plate has been shifted to the front to allow a better view of the locking system.
Figure 8:
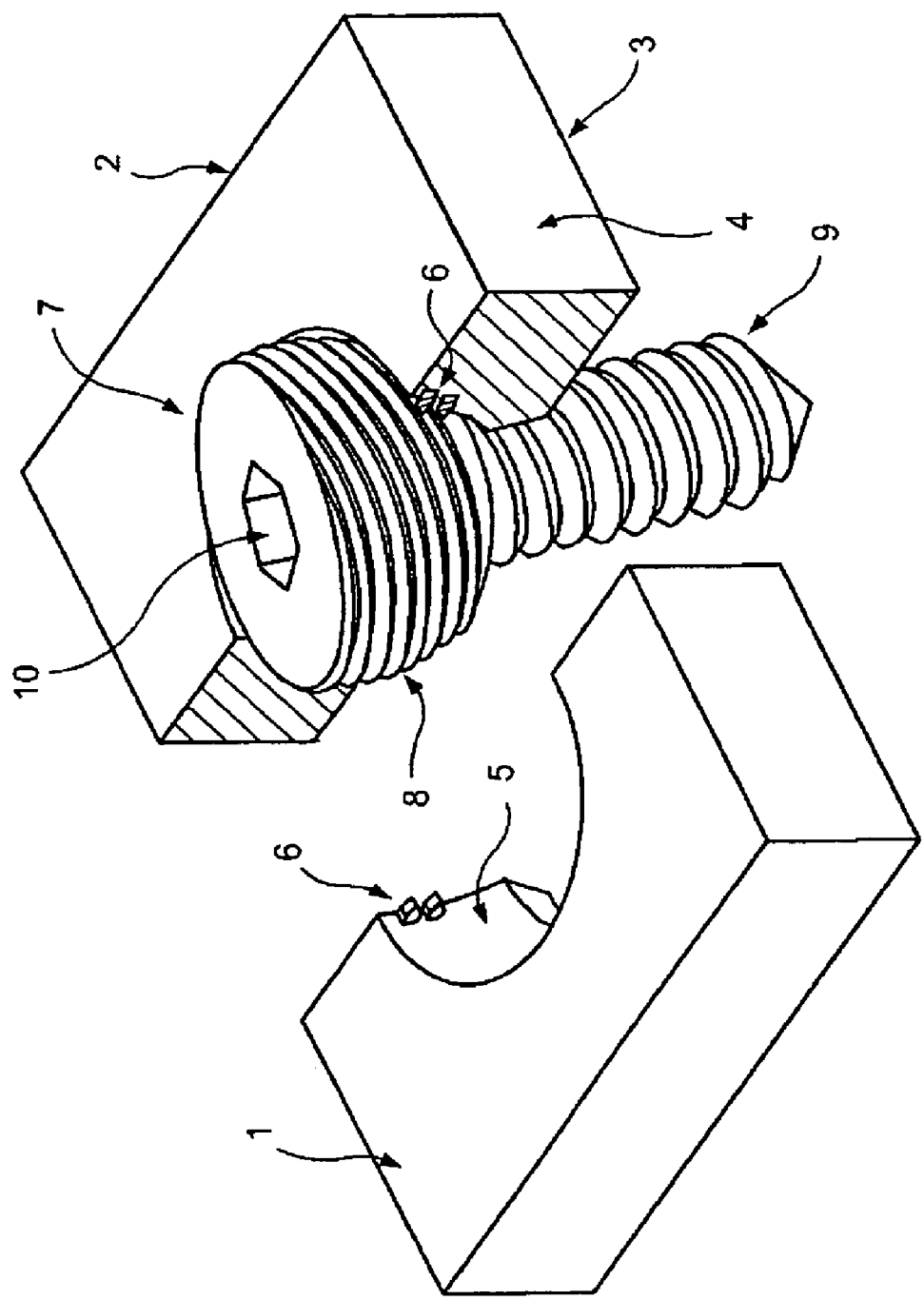
FIG. 8 is a perspective view of a bone fixation assembly according to the present invention wherein the screw is locked at a tilt, and wherein the anterior half of the plate has been shifted to the front to allow a better view of the locking system.
Figure 9:
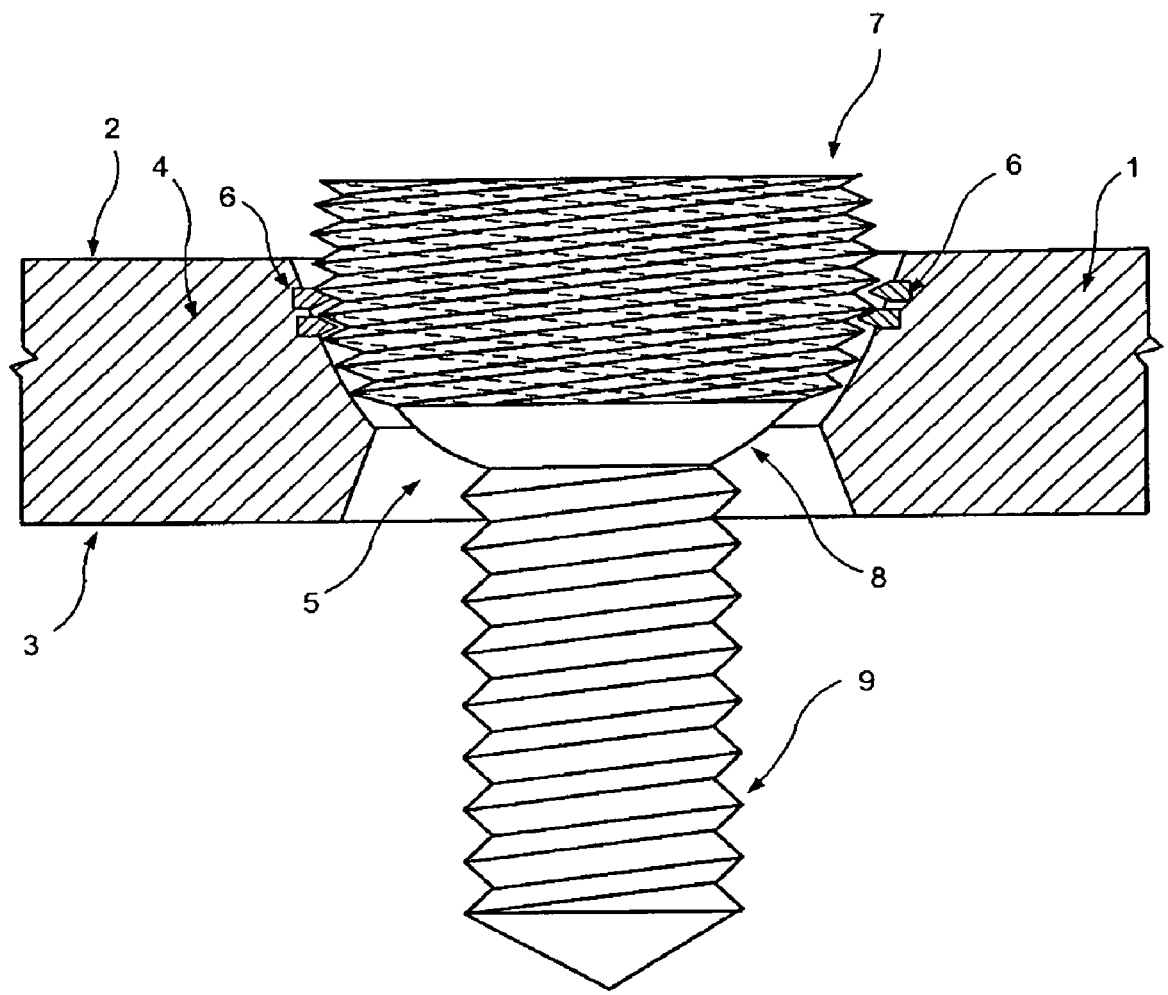
FIG. 9 is a front view of a bone fixation assembly according to the present invention wherein the screw is perpendicularly locked, and wherein the anterior half of the plate has been removed to allow a better view of the locking system.

As best seen in FIGS. 4, 5, and 6, plate holes 5 have an hourglass shape. The plate holes 5 are cut out of the bone plate 1 in a spherical shape, with both edges removed in a frustoconical shape. The easiest way to understand the shape of the plate holes 5 is to imagine two frustoconical holes connected by their tips through a partial sphere. The inner wall of each plate hole 5 has a small number of isolated protrusions 6 (such as pegs or spikes), which can number from 2 to 30, designed to lock against the threaded spherical head 8 of the screws when the screws 7 are driven in through the plate holes 5. The protrusions 6 in the preferred embodiment are somewhat flattened, having a width bigger than their length.

As it is shown in FIGS. 7, 8, 9, and 10 once the screw 7 has been driven in, it locks tightly against the protrusions 6 existing in the plate holes 5. It does not matter if the screw 7 was introduced perfectly perpendicular or at a tilt, the locking happens exactly the same way, only in different positions. This is possible because of the spherical shape of the screw head 8 allowing a good fit among the thread of the screw head 8 and the protrusions 6 in either perpendicular or tilted position. The amount of tilting accepted by this system varies according with the design. In the preferred embodiment shown through FIGS. 1 to 10, up to 20 degrees of angulation in any direction is allowed.

While I have illustrated and described a preferred embodiment of the invention, it will be understood that those skilled in the art will thereby be enabled to devise variations and modifications without departing from the spirit and scope of this invention, as defined in the appended claims. For example, the plate hole 5 of the fixation device could be a combination of a few frustocones. A screw 7 with its head shaped like a sphere, can be used in conjunction with a bone fixation device with a through hole 5 with a shape generated by a combination of a few frustocones. The same applies if a screw 7 with its head generated by a rotating polygonal line and a fixation device with its holes 5 cut out in a spherical shape are used. The protrusions 6 included on the inner wall of the plate hole 5 could be round instead of being flattened protrusions 6. Another variation could be related to the circular cross section of the protrusions 6 included on the inner wall of the plate hole 5 having the same width and length.

It must be noted that in every feasible embodiment, the hourglass shape of the plate hole 5 is mandatory in order to allow space for the screw 7 to be inserted at a tilt.

What I claim as my invention is:

1. A method for fixing bone comprising:
   providing a bone plate configured and dimensioned for application to a patient's bone, the plate having an upper surface, a lower surface and at least one opening extending from the upper surface to the lower surface, the opening defining a first axis substantially perpendicular to the upper surface and the opening, the opening provided with non-thread protrusions configured and dimensioned to have the same pitch and mate with the threads on a bone screw head, wherein the non-thread protrusions exhibit the same pitch as that of the bone screw head prior to insertion of the bone screw head into the opening;
   applying the bone plate to a patient's bone;
   inserting a bone screw through the opening in the bone plate at a selected, variable angle of rotation relative to the first axis, the bone screw having a threaded head portion, the threaded head portion having a double entry thread; and
   tightening the bone screw such that the threaded head portion of the screw mates with one or more of the protrusions of the inner surface of the opening in the bone plate to lock the screw to the plate at the selected angle relative to the first axis.

2. The method of claim 1, wherein the head of the bone screw is at least partially spherical.

3. The method of claim 1, wherein the bone screw includes a shank portion having threads, and the threads of the shank portion have substantially the same pitch as the threads of the head portion.

4. The method of claim 1, wherein the inner surface of the opening in the plate includes a first area having protrusions and a second area without protrusions and the second area is greater than the first area.

5. The method of claim 4, wherein the inner surface of the opening includes between about 2 and about 30 protrusions.

6. The method of claim 4, wherein the bone screw is self-drilling.

7. The method of claim 1, wherein the bone screw is self-tapping.

8. The method of claim 1, wherein the bone screw has a non-threaded shaft portion.

9. The method of claim 1, wherein the opening of the plate comprises a plurality of frustoconical holes that form an hourglass shape, and each protrusion formed on the inner surface of the opening has a flat shape with a width greater than its length.

10. The method of claim 1, wherein at least some of the protrusions are substantially wedge-shaped.

11. The method of claim 1, wherein at least some of the protrusions are symmetrically distributed in a plane along a circumference of the inner surface of the opening.

12. The method of claim 1, wherein the protrusions are distributed in two substantially parallel planes along the inner surface of the opening.

13. The method of claim 1, wherein the angle of orientation of the bone screw relative to the first axis may vary from about zero degrees to about twenty degrees.

14. The method of claim 1, wherein each of the protrusions includes one of a peg and a spike.

15. A method of fixing bone whereby a fixation device having at least one opening is secured to at patient's bone using a threaded bone engaging member, the method comprising:
    applying the fixation device to the patient's bone;
    selecting an angle of orientation of the bone engaging member relative to the fixation device;
    threading the bone engaging member through the opening at the selected angle of orientation with respect to the fixation device;
    threading a double-entry threaded head of the bone engaging member onto non-thread protrusions formed on an inner surface of the opening, the protrusions configured and dimensioned to have the same pitch and mate with the double-entry threads for the head of the bone engaging member at the selected angle of orientation, wherein the protrusions exhibit the same pitch as the double-entry threads prior to the threading of the double-entry threaded head; and
    tightening the bone engaging member to rigidly lock the bone engaging member at the selected angle of orientation with respect to the fixation device without using any additional, separate components at an interface between the bone engaging member and the fixation device.

16. The method of claim 15, wherein the head of the bone engaging member is partially spherical and the bone engaging member includes a threaded shank, and the threads of the head and the shank have substantially the same pitch.

17. The method of claim 15, wherein the protrusions are formed on the inner surface of the opening near the top of the opening.

18. The method of claim 15, wherein the inner surface of the opening in the fixation device includes a first area having protrusions and a second area without protrusions and the second area is greater than the first area.

19. The method of claim 15, wherein the fixation device includes between about 2 and about 30 protrusions.

20. The method of claim 15, wherein the opening of the fixation device comprises a plurality of frustoconical holes that form an hourglass shape, and each protrusion formed on the inner surface of the opening has a flat shape with a width greater than its length.

21. The method of claim 15, wherein the protrusions are substantially wedge-shaped.

22. The method of claim 15, wherein at least some of the protrusions are symmetrically distributed in a plane along a circumference of the inner surface of the opening.

23. The method of claim 15, wherein the protrusions are distributed in two substantially parallel planes along the inner surface of the opening.

24. The method of claim 15, wherein the angle of orientation of the bone engaging member relative to the fixation device may vary from about zero degrees to about twenty degrees.

25. The system of claim 24, wherein the protrusions are configured and dimensioned to lock the bone fixation member relative to the fixation device at a variable angle of orientation of between about zero degrees and about twenty degrees.

26. The method of claim 15, wherein each oft. protrusions includes one of a peg and a spike.

27. A bone fixation system comprising:
    a fixation device configured and dimensioned for application to a patient's bone, the fixation device having an upper surface, a lower surface and at least one opening extending from the upper surface to the lower surface, the opening defining a first axis substantially perpendicular to the upper surface and the opening including a plurality of isolated, non-thread protrusions formed on an inner surface of the opening, the protrusions configured and dimensioned to have the same pitch and mate with threads on a bone engaging member; and
    a bone engaging member configured and dimensioned for insertion through the opening in the fixation device at a selected angle of orientation relative to the first axis, the bone engaging member having a threaded head portion, the threaded head portion having a double entry;
    wherein upon tightening of the bone engaging member, the threaded head portion of the bone engaging member mates with one or more protrusions of the inner surface of the fixation device opening to lock the bone engaging member to the plate at the selected angle of orientation relative to the first axis, and wherein the protrusions exhibit the same pitch as the threads on the bone engaging member prior to insertion of the bone engaging member in the opening.

28. The system of claim 27, therein the fixation device is a bone plate and the bone engaging member is a bone screw.

29. The system of claim 28, wherein the head of the bone screw is at least partially spherical.

30. The system of claim 29, wherein the bone screw includes a shank portion having threads, the threads of the shank portion have substantially the same pitch as the threads of the head portion.

31. The system of claim 27, wherein the inner surface of the opening in the fixation device includes a first area having protrusions and a second area without protrusions and the second area is greater than the first area.

32. The system of claim 31, wherein the inner surface of the opening includes between about 2 and about 30 protrusions.

33. The system of claim 27, wherein the opening of the fixation device comprises a plurality of frustoconical holes that form an hourglass shape, and each protrusion formed on the inner surface of the opening has a flat shape with a width greater than its length.

34. The system of claim 27, wherein the protrusions are substantially wedge-shaped.

35. The system of claim 27, wherein at least some of the protrusions are symmetrically distributed in a plane along a circumference of the inner surface of the opening of the fixation device.

36. The system of claim 27, wherein the protrusions are configured and dimensioned lock the bone fixation member relative to the fixation device at a variable angle of orientation of between about zero degrees and about twenty degrees.

37. The system of claim 27, wherein each of the protrusions includes one of a peg and a spike.

* * * * *

UNITED STATES PATENT AND TRADEMARK OFFICE
CERTIFICATE OF CORRECTION

PATENT NO. : 7,637,928 B2 Page 1 of 1
APPLICATION NO. : 10/763689
DATED : December 29, 2009
INVENTOR(S) : Alberto Angel Fernandez It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1138 days.

Signed and Sealed this

Ninth Day of November, 2010

David J. Kappos
*Director of the United States Patent and Trademark Office*